US006532978B1

(12) United States Patent
Müller-Kuhrt et al.

(10) Patent No.: US 6,532,978 B1
(45) Date of Patent: Mar. 18, 2003

(54) METHOD AND DEVICE FOR REGULATING INDIVIDUAL SUB-FLOWS OF A SYSTEM FOR CONVEYING FLUID MEDIA

(75) Inventors: Lutz Müller-Kuhrt, Berlin (DE); Ralf God, Berlin (DE); Holger Gumm, Berlin (DE); Jörg Binkele, Potsdam (DE)

(73) Assignee: SEPIAtec GmbH, Potsdam (DE)

( * ) Notice: Subject to any disclaimer, the term of this patent is extended or adjusted under 35 U.S.C. 154(b) by 0 days.

(21) Appl. No.: 09/856,131

(22) PCT Filed: Nov. 22, 1999

(86) PCT No.: PCT/EP99/09748
§ 371 (c)(1),
(2), (4) Date: Aug. 6, 2001

(87) PCT Pub. No.: WO00/31602
PCT Pub. Date: Jun. 2, 2000

(30) Foreign Application Priority Data

Nov. 20, 1998 (DE) .......................... 198 55 002

(51) Int. Cl.⁷ .......................... G05D 7/06; G05D 11/00
(52) U.S. Cl. .................. 137/1; 137/118.04; 137/487.5; 137/883
(58) Field of Search ................ 137/1, 118.04, 137/118.06, 487.5, 599.01, 599.05, 599.06, 883

(56) References Cited

U.S. PATENT DOCUMENTS

| | | | | |
|---|---|---|---|---|
| 2,676,603 A | * | 4/1954 | Kollsman | 137/118.06 |
| 4,065,250 A | * | 12/1977 | Schliefer et al. | 432/24 |
| 4,190,084 A | * | 2/1980 | Harrison | 137/883 |
| 4,191,215 A | * | 3/1980 | Gonner | 137/870 |
| 4,640,310 A | * | 2/1987 | Hartle et al. | 137/883 |
| 5,992,453 A | * | 11/1999 | Zimmer | 137/561 A |
| 6,036,107 A | * | 3/2000 | Aspen et al. | 239/170 |

FOREIGN PATENT DOCUMENTS

| | | | |
|---|---|---|---|
| GB | 2 275 115 A | * | 8/1994 |
| WO | WO 98 37790 A | * | 9/1998 |

OTHER PUBLICATIONS

International Search Report for corresponding PCT application PCT/EP 99/09748 dated Mar. 24, 2000.*
International Preliminary Examination Report for PCT/EP 99/09748 dated Mar. 1, 2001.*

* cited by examiner

Primary Examiner—Michael Powell Buiz
Assistant Examiner—Ramesh Krishnamurthy
(74) Attorney, Agent, or Firm—Norris McLaughlin & Marcus (57) ABSTRACT

The invention relates a method and a device for regulating individual sub-flows of a conveying system while the main flow is conveyed in a constant manner. The aim of the invention is to provide a method and a device which enable the sub-flows of the conveying lines of a system for conveying fluid media to be regulated as required in said individual conveying lines with just one conveyor unit. To this end, the inventive device for regulating individual sub-flows of a system for conveying fluid media has several conveying lines which are guided in parallel. The invention is characterized in that the following are arranged in the conveying system: at least one total pressure measuring device (10), at least one sub-flow measuring unit (D) in each conveying line, at least one valve (7) with a throttle (B) and a data acquisition, processing and control value output module (C), these being functionally interconnected by hardware and/or software.

19 Claims, 11 Drawing Sheets

METHOD AND DEVICE FOR REGULATING INDIVIDUAL SUB-FLOWS OF A SYSTEM FOR CONVEYING FLUID MEDIA

BACKGROUND OF THE INVENTION

The invention relates to a method and a device for regulating individual sub-flows of a system for conveying fluid media in accordance with the introductory portion of claims 1 and 7.

In systems for conveying fluid media with several parallel conveying lines, the generation of pressure is responsible for the transport of the medium. Frequently, it is necessary that the individual sub-flows, arriving at the respective conveying destination, are of the same or of a known magnitude. In such a case, it must be possible to adjust the deviating flow resistances.

The possibility of temporally coordinating the volumes (or masses), arriving at the conveying destination, is particularly important if the composition of the fluid medium is selectively inhomogeneous or if the fluid medium is a carrier for substances, which are to be transported discontinuously. Even if, during the conveying of liquid media, exact quantitative doses or also analytical determinations of a possibly changing composition in the individual conveying lines of a conveying system are required, unforeseeable flow rate times can create problems. For example, in the area of the food industry, of medical technology and also of the pharmaceutical industry, it is frequently necessary to supply certain volumes simultaneously to a particular conveying destination. In practice, different and, in some cases also, temporally changing flow resistances in the individual conveying lines stand in the way of this necessity. These different flow resistances arise due to different frictional losses in the line system and result, for example, from material defects, different flow cross sections or also blockages. For example, in the area of the food industry, of medical technology and also of the pharmaceutical industry, it is frequently necessary to supply certain volumes simultaneously to a particular conveying destination. In practice, different and, in some cases also, temporally changing flow resistances in the individual conveying lines stand in the way of this necessity. These different flow resistances arise due to different frictional losses in the line system and result, for example, from material defects, different flow cross sections or also blockages.

Until now, only the control of the pressure in the individual conveying lines was known. An example of this is shown in the U.S. Pat. No. 2,676,603. The apparatus, shown there, works with several restricting capillaries, which are brought to the same pressure level at the outlet side. The volume flows emitted are the same only at identical pressures in the discharging chambers described there, at identical pre-pressure, at identical temperature and with identical restricting capillaries. The control namely functions only if the respective counter-pressures of the units, which are to be supplied (in the case shown there of an internal combustion engine, the pressure drop at the fuel pipelines plus the drop in the intake manifold when the inlet valve is opened), are small in comparison to the regulator dwell pressure. If these counter pressures exceed a certain limiting value, the control is made inoperative and the volume flows adjust corresponding to the respective counter-pressure. In addition, the control does not notice if one of the restricting capillaries has an increased flow resistance, for example, because of a blockage. In the blocked restricting capillary, there is then a correspondingly smaller volume flow, while the pressure drop is the same.

SUMMARY OF THE INVENTION

It is an object of the invention to provide a method and a device, with which it is possible to regulate the sub-flows of the individual conveying lines of a conveying system for fluid media, as required, with only a single constant conveying unit.

This objective is accomplished with the characterizing distinguishing features of claims 1 and 7.

Advantageous further developments are given in the dependent claims.

An essential distinguishing feature of the method described here is the determination of partial flow resistances from the ratio of a total pressure P, measured before the distribution, and a sub-flow value $S_n$, determined in each conveying line. The latter could not be attained without including the total pressure and the direct control on the sub-flow at constant total flow.

For the selection of the total pressure sensor, which determines the pressure P ahead of the distribution over the individual conveying lines, the permissible range of the total flow, as well as the possible changes in the viscosity of the conveying medium are of decisive importance. The selection of an advantageous measurement principle for determining the sub-flow value $S_n$ depends on the particular application.

Different methods are known for measuring volume and mass flows. Criteria for the selection of flow-through measuring devices are set down in DIN 2644.

The advantages of the invention lie in the possibility of producing with the method and the device identical or selectively different sub-flows for fluid media in the conveying lines in a conveying system using a single conveying unit (such as a pump).

Each of the control devices, working strandwise, can undertake the approach of the actual value to the specified value without interference from the control processes in the other conveying lines. In contrast to this, with direct regulation of the sub-flows using a flow meter and a control valve, interference by the control processes in the other conveying lines would be unavoidable. Overall, because a constant flow is supplied, it would not be possible to control the sub-flow.

For the methods described, the conveying output and conveying pressure can be varied without disturbing the controlled equilibrium. For applications with a viscosity that varies, the specified value can be adjusted independently of the viscosity by a suitable selection and a suitable installation of the sub-flow unit.

A further, important advantage of the invention consists of determining changes in the flow resistance of individual conveying lines, which occur suddenly or slowly during the operation, for example, due to blockages during the transport of dispersions or in the case of leaks in a conveying line. If a permitted control value range is set for the valve used, the above-mentioned disturbances can be noted in good time and the conveying lines in question switched out.

BRIEF DESCRIPTION OF THE DRAWINGS

The invention is explained in greater detail in the following by means of examples and drawings, in which.

DESCRIPTION OF THE PREFERRED EMBODIMENT

In FIGS. 1a to 1d, an inventive regulating device is described diagrammatically. It is disposed in a conveying line 11 of a multi-channel conveying system and the course of its functioning is shown. For purposes of clarity, only conveying line. 11 is shown here for explaining the device.

Figure 1A:
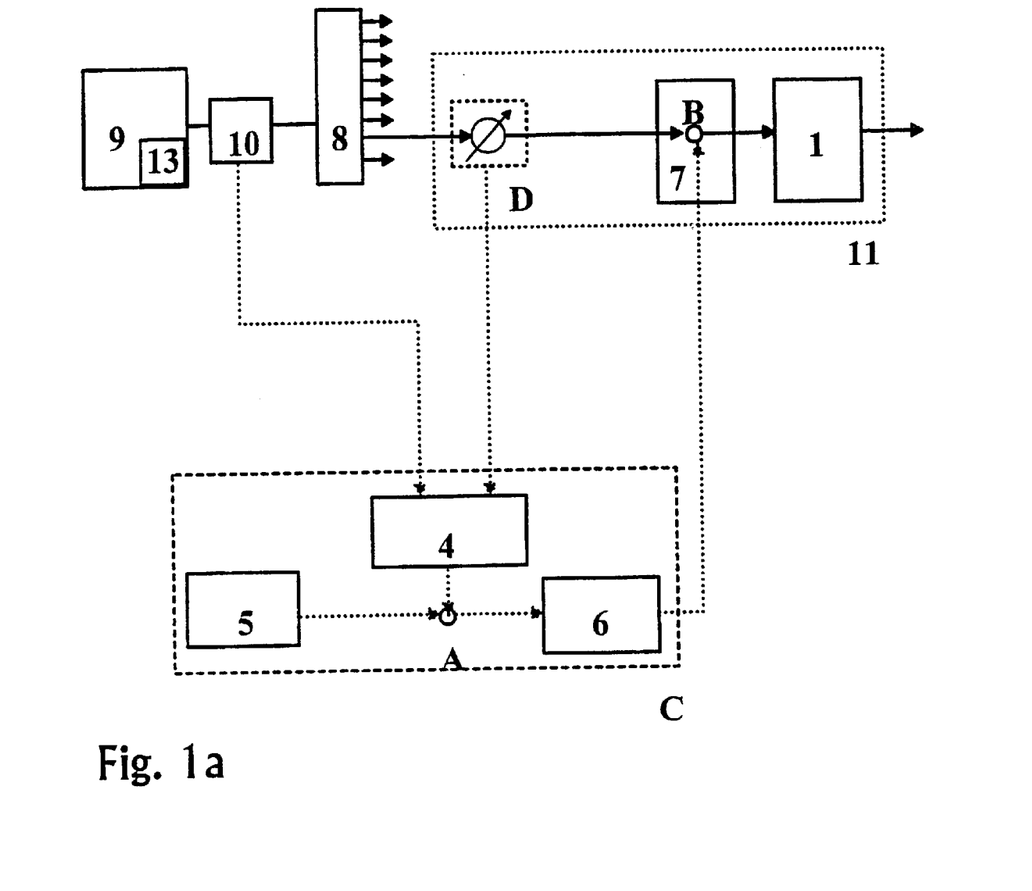
FIG. 1a shows a first diagrammatic representation of the arrangement of the regulating device in a conveying line, the sub-flow unit and the throttling site B of the valve (7) being disposed ahead of the flow resistance, FIG. 1b a second diagrammatic representation of the arrangement of the regulating device in a conveying line, the sub-flow unit and the throttling site B of the valve (7) being disposed behind the flow resistance, FIG. 1c a third diagrammatic representation of the arrangement of the regulating device in a conveying line, the sub-flow unit being disposed ahead of and the throttling site B of the valve (7) being disposed behind of the flow resistance.

The total pressure, produced by a conveying unit 9 (with constant flow control 13 of the conveying system, drives a sub-flow of a fluid phase (medium) for the conveying line 11 in question. In FIG. 1a, this sub-flow, after the distribution 8 through the sub-flow measuring unit D and, after that, over the throttling site B of the valve 7, flows through the flow resistance 1. A total pressure measuring device 10, which is disposed at the outlet side of the conveying unit 9, determines the pressure P, dropping off at the total system. The ratio of this pressure to a sub-flow value $S_n$, determined in each conveying line 11, represents an actual value of the flow resistance numeral 1 for the conveying line under consideration. In the actual value determination 4 of the data acquisition, processing and control value output module C, this ratio is calculated as actual value and supplied to the comparison site A (actual value—specified value) of the data acquisition processing and control value output module C. From the so-called actual value and a value specified by a specified value output part 5, a control difference is calculated, which controls the control process over the controller 6 and the valve 7.

Figure 1B:
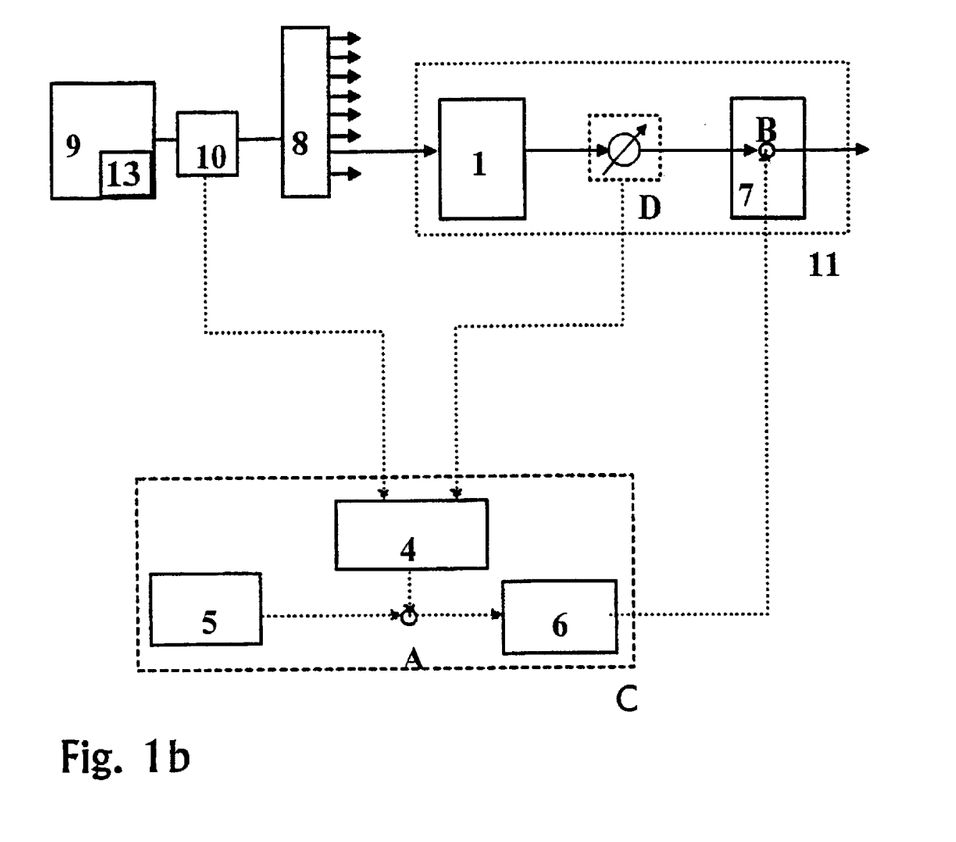
Figure 1C:
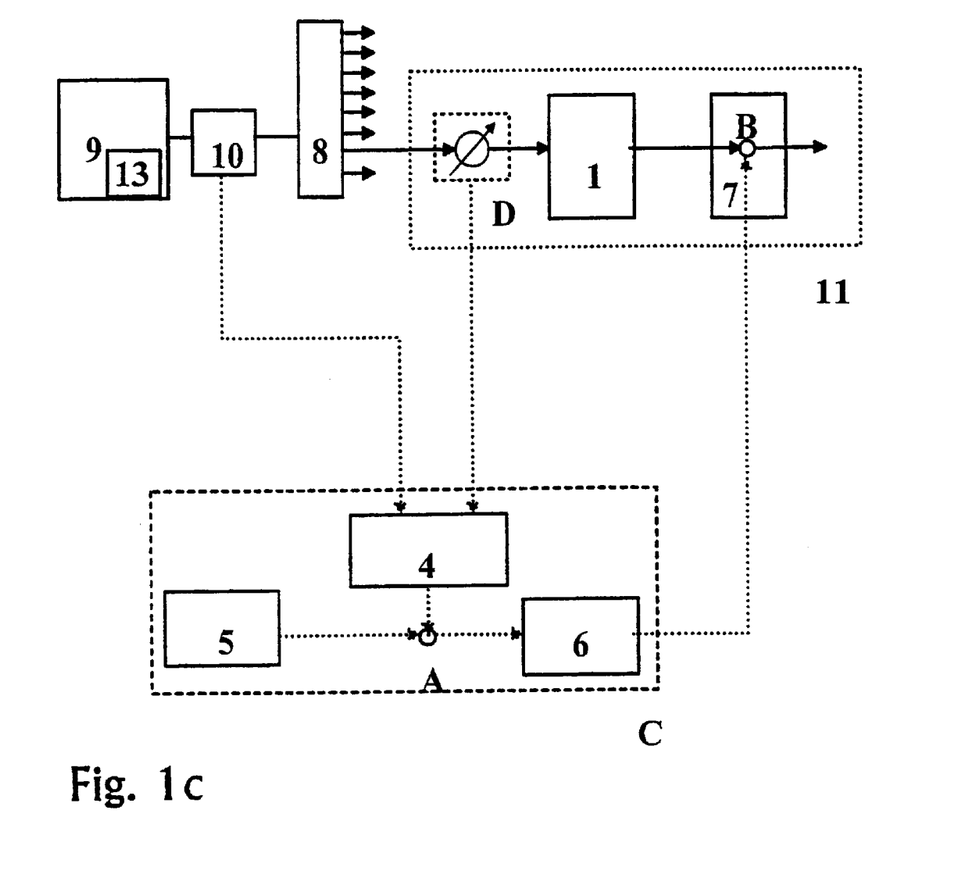
Figure 1D:
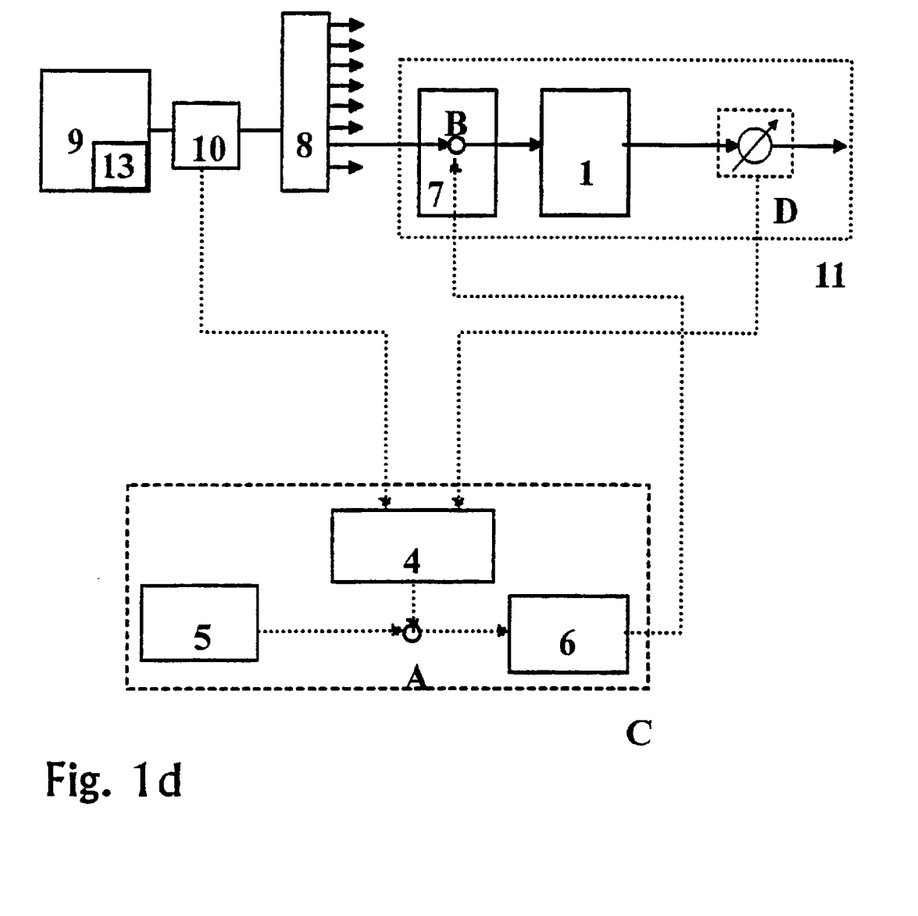
FIG. 1d shows a fourth diagrammatic representation of the arrangement of the regulating device in a conveying line, the sub-flow unit being disposed behind and the throttling site B of the valve (7) being disposed ahead of the flow resistance.

FIGS. 1b to 1d shows further possible variations of the arrangement for this embodiment of the invention.

Figure 2A:
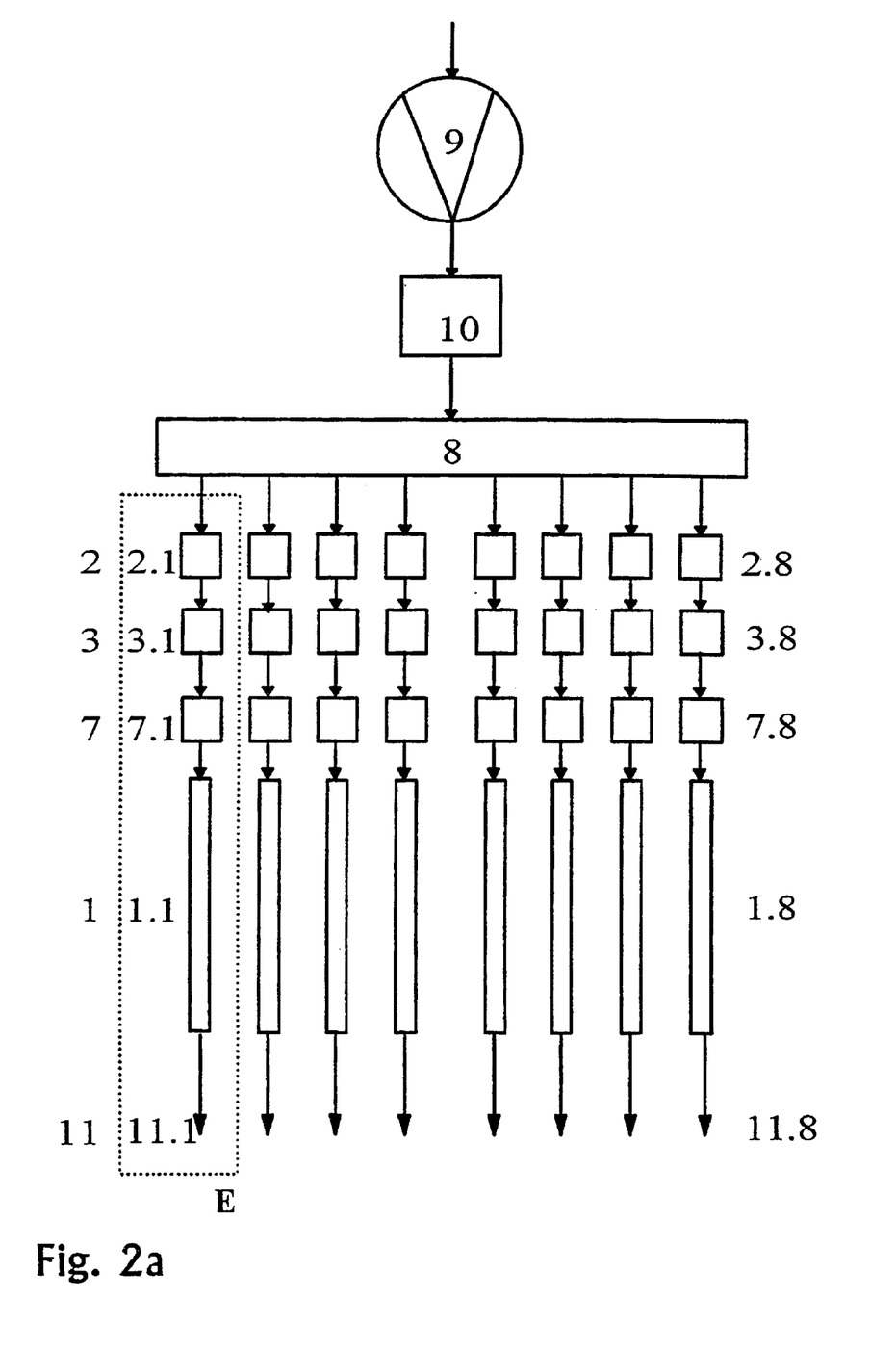
FIG. 2a shows a first diagrammatic variation of the arrangement of the regulating device with sub-flow measurement by pressure difference in a conveying system.

In accordance with a further embodiment of the invention shown in FIGS. 2a to 2f, the sub-flow is determined by means of a pressure drop, which is directly proportional to the sub-flow, at a measurement capillary 2, which is disposed serially to the flow resistance numeral 1. This pressure drop is determined from the difference between two precious. In a preferred variation of the arrangement of this special embodiment of the invention, which is shown in FIG. 2a, this pressure drop is represented by the difference between the pressure at the total pressure metering device 10 and the partial pressure metering device 3 ($\Delta P_{measurement\ capillary} = P - P_{measurement\ capillary}$). The above ratio therefore is calculated accordingly from the total pressure P and the pressure difference at the measurement capillary.

FIG. 2b to FIG. 2f shows further possible variations of this special embodiment of the invention.

The special embodiment mentioned (FIG. 2a to FIG. 2f) with measurement of the sub-flow by measuring the difference in pressure, because of this special importance for the control method described, are explained in greater detail below for equipment with eight conveying lines.

The conveyed liquid phase is distributed by means of a distributor 8 to, for example, eight conveying lines, which extend parallel to one another. In each conveying line, flow resistances 1.1 to 1.8 are shown diagrammatically.

In the above-mentioned preferred special variation of the invention of FIG. 2a, the valves 7.1 to 7.8, the partial pressure measuring devices 3.1 to 3.8 and the measurement capillaries 2.1 to 2.8 are ahead of the respective flow resistance 1.1 to 1.8

Figure 2B:
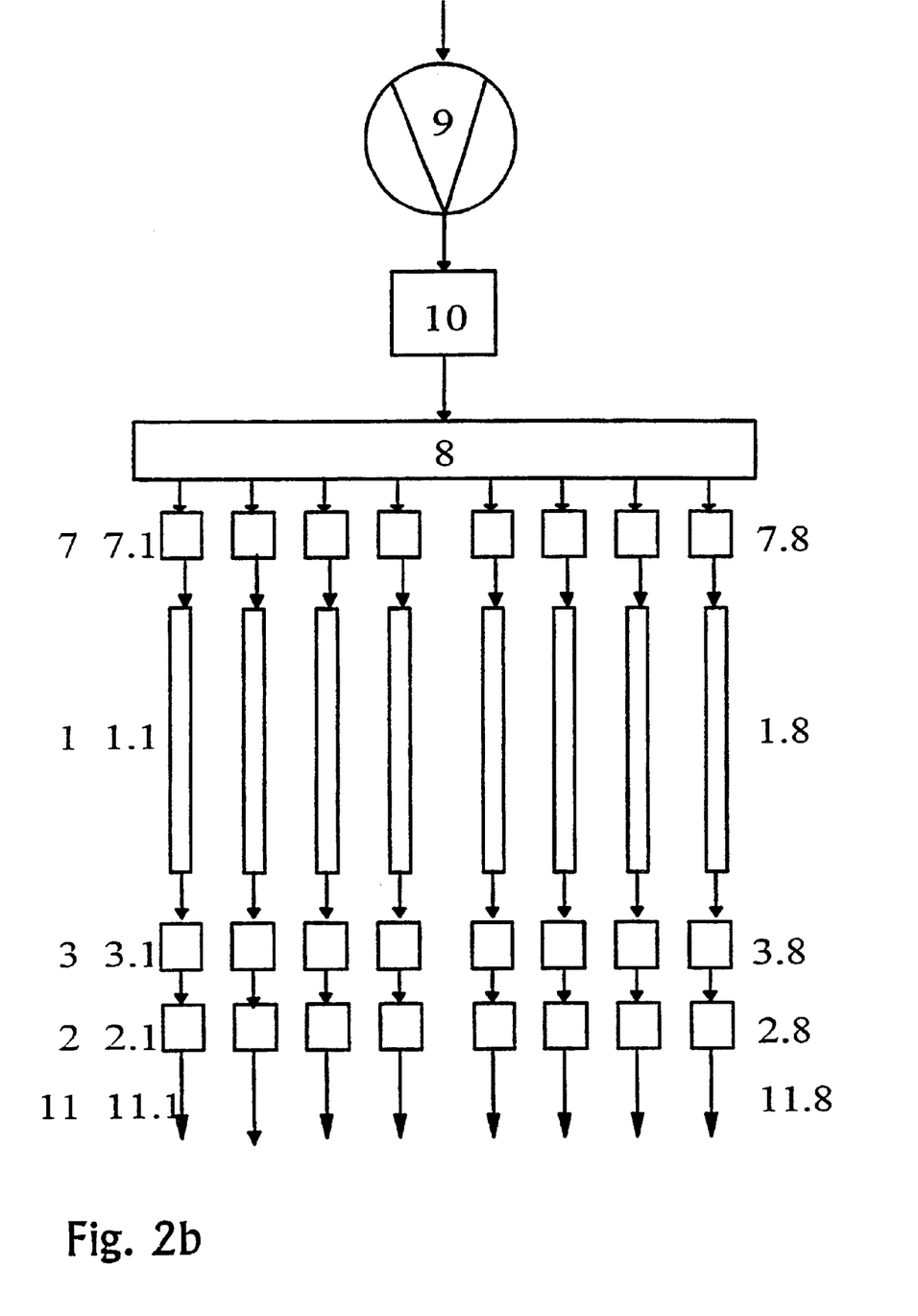
FIG. 2b shows a second diagrammatic variation of the arrangement of the regulating device with sub-flow measurement by pressure difference in a conveying system.

In FIG. 2b, the valves 7.1 to 7.8 are disposed at the inlet side and the partial pressure measuring devices 3.1 to 3.8, as well as the measurement capillaries 2.1 to 2.8 are disposed at the outlet side of the flow resistances 1.1 to 1.8. The measurement capillaries here are at the outlet side at the same pressure level (such as atmospheric pressure).

Figure 2C:
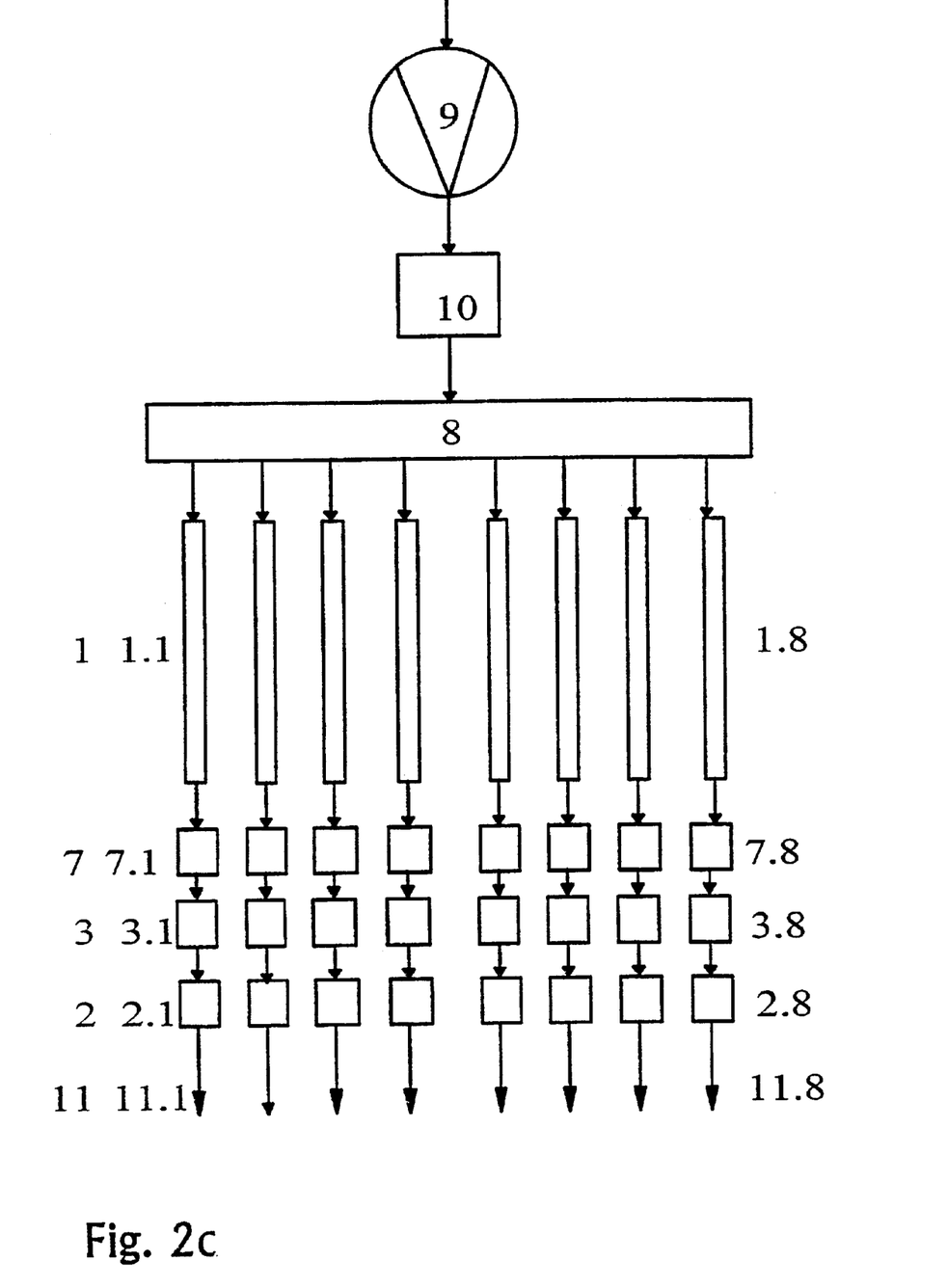
FIG. 2c shows a third diagrammatic variation of the arrangement of the regulating device with sub-flow measurement by pressure difference in a conveying system.

According to FIG. 2c, the complete arrangement of the partial pressure measuring devices 3.1 to 3.8, the measurement capillaries 2.1 to 2.8 and of the valves 7.1 to 7.8 is also possible at the outlet side of the flow resistances 1.1 to 1.8. Moreover, the measurement capillaries at the outlet side are at the same pressure level (such as atmospheric pressure).

Figure 2D:
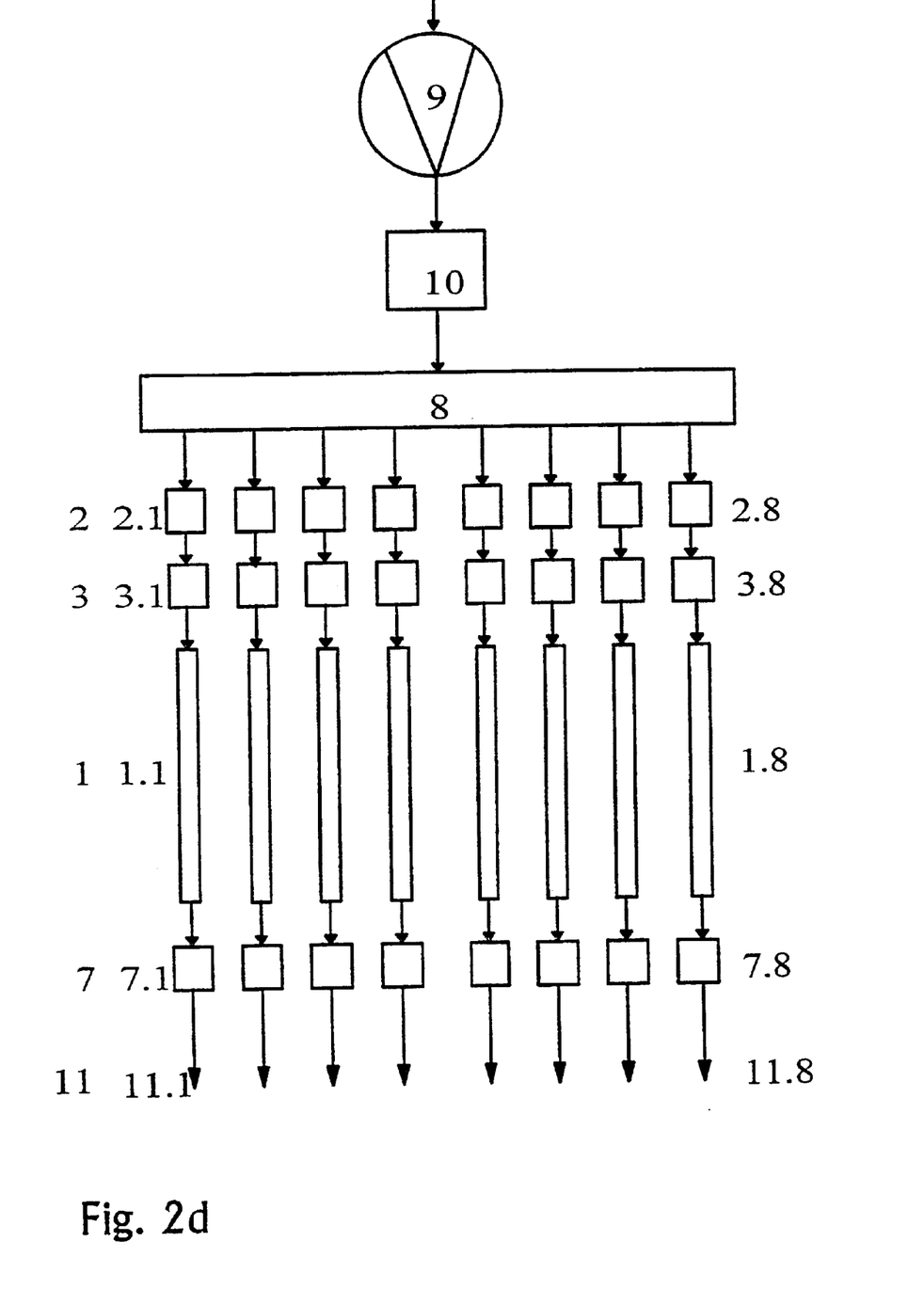
FIG. 2d shows a fourth diagrammatic variation of the arrangement of the regulating device with sub-flow measurement by pressure difference in a conveying system.

In any further variation, shown in FIG. 2d, in a reversal of the arrangement of FIG. 2b, the possibility is provided pursuant to the invention of disposing the partial pressure metering devices 3.1 to 3.8 and the measurement capillaries 2.1 to 2.8 at the inlet side and the valves 7.1 to 7.8 at the outlet side of the flow resistances 1.1 to 1.8. The measurement capillaries here are at the inlet side at the same total pressure level, which is measured by the total pressure measuring device 10 ahead of the distribution.

Figure 2E:
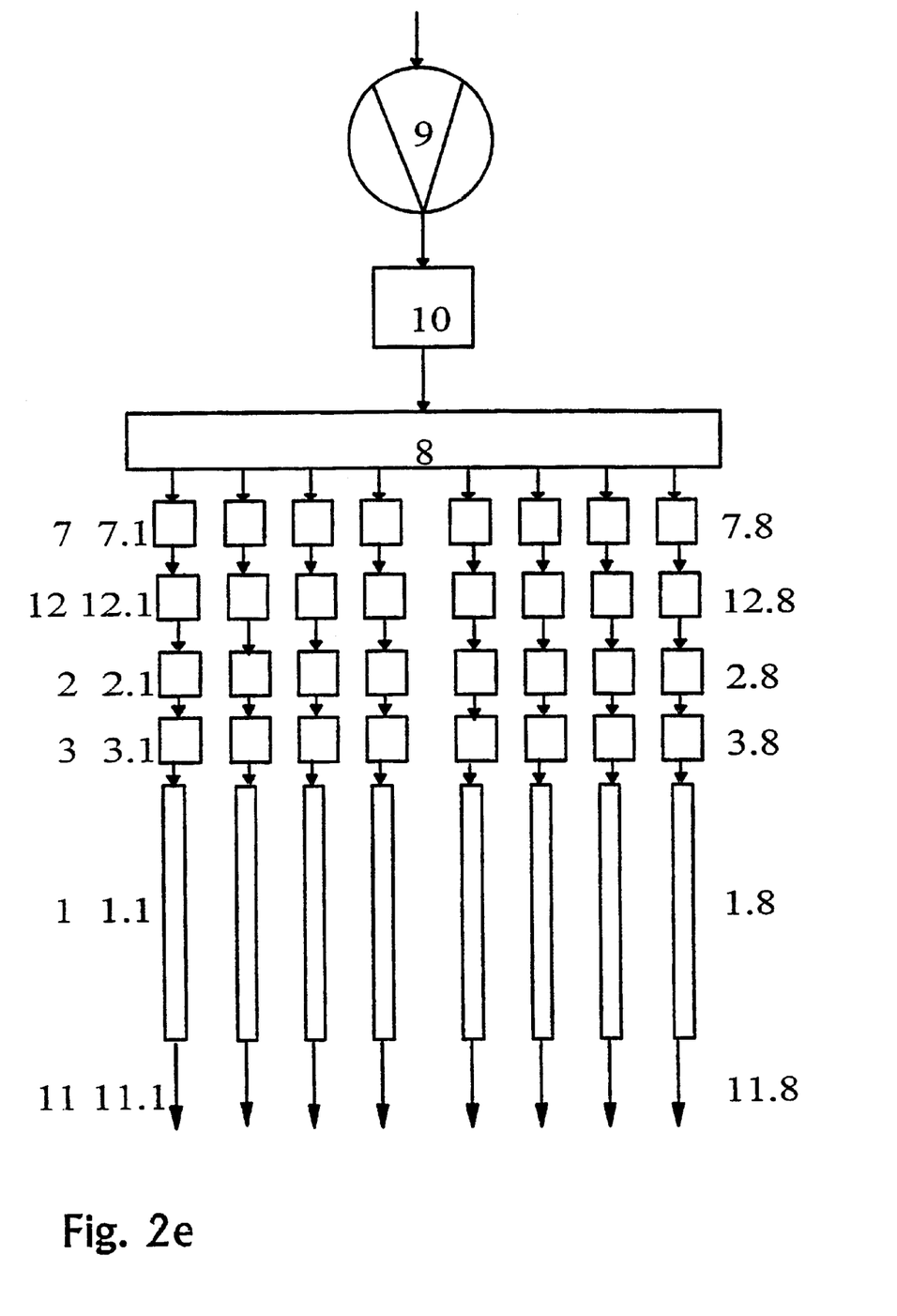
FIG. 2e shows a fifth diagrammatic variation of the arrangement of the regulating device with sub-flow measurement by pressure difference in a conveying system.

According to FIG. 2e, the valves 7.1 to 7.8 and the measurement capillaries 2.1 to 2.8 are disposed at the input side of the flow resistances 1.1 to 1.8. The pressure drop at the measurement capillaries is determined in each case by means of two separate partial pressure measuring devices of the same type 12.1 to 12.8 and 3.1 to 3.8.

Figure 2F:
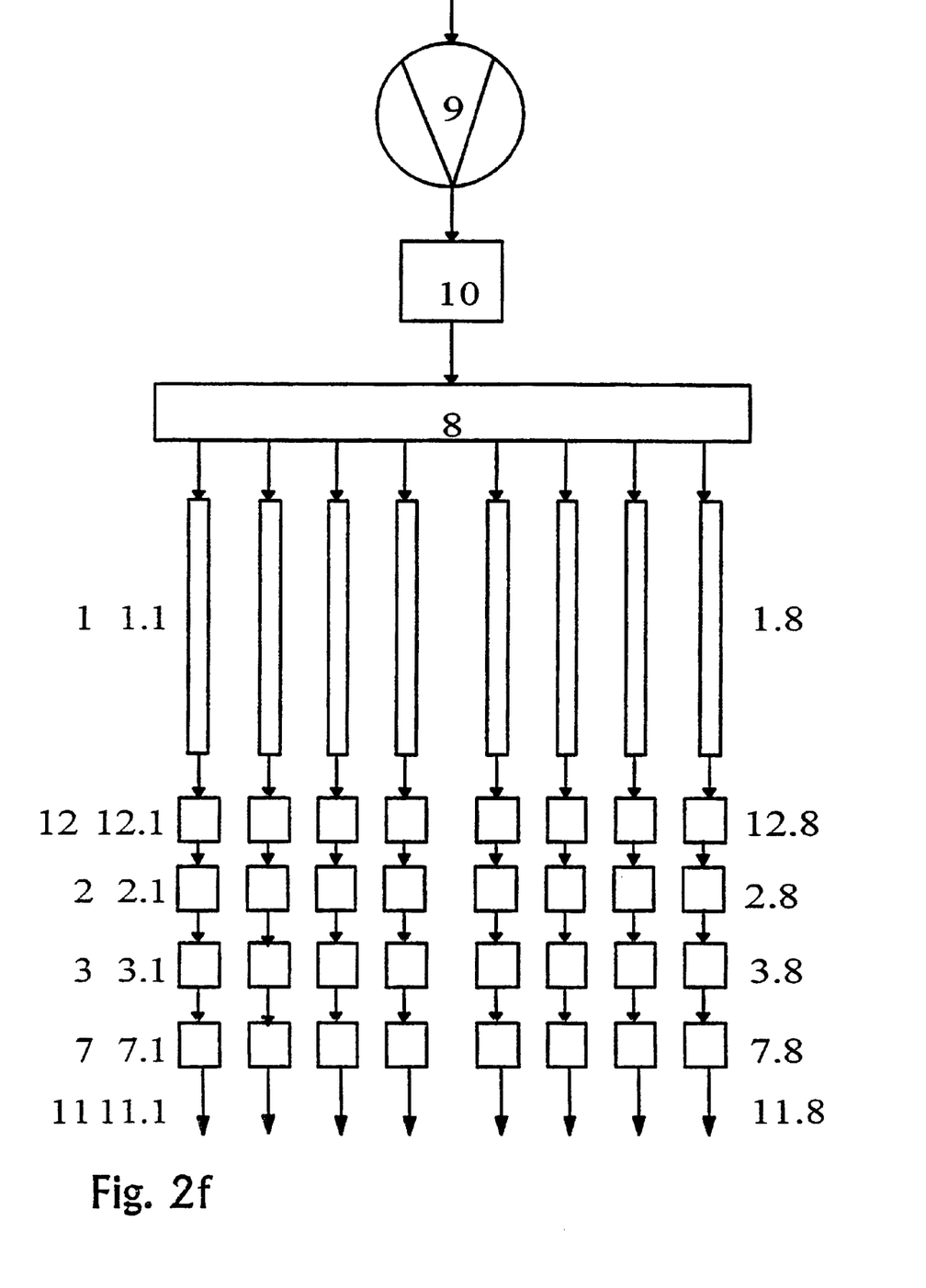
FIG. 2f shows a sixth diagrammatic variation of the arrangement of the regulating device with sub-flow measurement by pressure difference in a conveying system.

A further exchange of the measurement capillaries 2.1 to 2.8, disposed at the outlet side of the flow resistances, and of the valves 7.1 to 7.8 in FIG. 2f, with respect to the representation of FIG. 2c, is possible. The pressure drop at the measurement capillaries (difference in pressure) is determined in each case by means of two separate partial pressure metering devices of the same type 12.1 to 12.8 and 3.1 to 3.8.

The embodiments of the inventive device, shown in FIG. 2a, FIG. 2d and FIG. 2e, are suitable especially for the operation with a fluid medium of changing viscosity, since the sites where the total pressure and partial pressure are measured, are spatially close to one another.

This possibility of arranging the regulating devise in a conveying system flexibly is associated with many advantages with respect to the structure for different fields of application.

Figure 3:
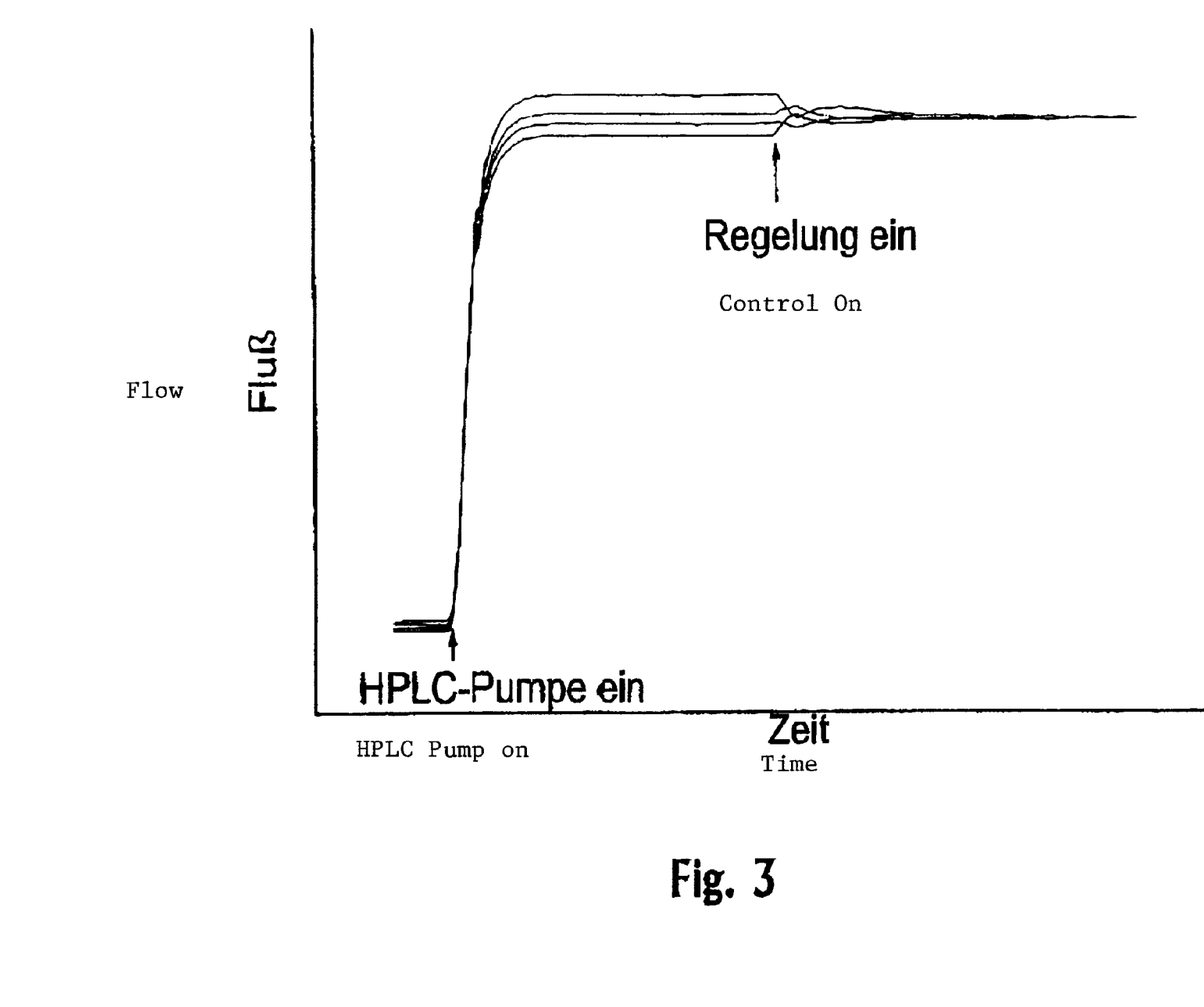
FIG. 3 shows a graphic representation of an indirect regulation of the volume flow, realized with a variation of the arrangement of FIG. 2a, in a four-channel liquid chromatography device.

In FIG. 3, the volume flows of four parallel separating lines of a liquid chromatograph are shown. The curves show the advantageous effect of the inventive, indirect volume flow control. The values of four different volume flows in single conveying lines rapidly approach a common value when and the control is switched on.

Since a sub-flow determination by measuring the difference in pressure at a measurement capillary is advantageous for many applications, a computational model is given in below for this already mentioned special, preferred embodiment of FIG. 2a. A consideration of the simple physical laws makes the relationships clear. It is assumed that the flow of the liquid is laminar and obeys the linear flow law. For an understanding, it is sufficient to describe only a single conveying line of n conveying lines. A conveying line consists, in this connection, consists of an arrangement for measuring the sub-flows by means of a measurement capillary, a valve for controlling and a main flow resistance. In the simplest case, it is assumed that there is one pipeline for this flow resistance (the corresponding applies for other flow resistances). $R_{index}$ refers to the flow resistances, $\Delta p$ to the pressure drops, $\eta$ to the viscosity of the liquid medium and V to the volume flow. (Further abbreviations will be explained with the formulas).

For the individual flow resistances of the considered conveying line E of the conveying system shown in FIG. 2a, the following expressions result:

$$R_{\text{measurement capillary (2.1)}} = \frac{\Delta P_{\text{measurement capillary}}}{V_{\text{sub}}} = \frac{8\eta l}{\pi r^4}$$

in which l=the length of the capillary and r=the internal radius of the capillary $$R_{\text{valve (7.1)}} = \frac{\Delta P_{\text{valve}}}{V_{\text{sub}}} = \frac{6\eta}{\pi s^3} G$$

in which s=the gap width, G=a geometric factor (depending on the type of valve)

$$R_{\text{pipeline (1.1)}} = \frac{\Delta P_{\text{pipeline}}}{V_{\text{sub}}} = \frac{8\eta L}{\pi R^4}$$

in which L length of the pipeline and R=the internal radius of the pipeline

With the resulting total pressure ahead of the distribution $$P = \Delta P_{\text{measurement capillary}} + \Delta P_{\text{valve}} + \Delta P_{\text{pipeline}}$$

it is possible to write for the total flow resistance $R_{\text{total}}$ of the conveying line in question $$R_{\text{total}} = \frac{P}{V_{\text{sub}}} = \frac{8\eta l}{\pi r^4} + \frac{6\eta}{\pi s^3} G + \frac{8\eta L}{\pi R^4}$$

Since $$V_{\text{sub}} = \frac{\pi r^4}{8\eta l} \Delta P_{\text{measurement capillary}} = \frac{\pi r^4}{8\eta l}(P - P_{\text{measurement capillary}})$$

the following can be written for the total flow resistance of the conveying line:

$$R_{\text{total}} = \left(\frac{8\eta l}{\pi r^4}\right) \frac{P}{P - P_{\text{measurement capillary}}} = R_{\text{measurement capillary}} + R_{\text{valve}} + R_{\text{pipeline}}$$

If the temperature is the same everywhere in the equipment, the viscosity $\eta = f(T) = $ const. can be eliminated from all the elements and the following relationship results $$R_{\text{total}} = \frac{P}{P - P_{\text{measurement capillary1}}} \frac{\pi r^4}{8l} \left(\frac{8l}{\pi r^4} + \frac{6G}{\pi s^3} + \frac{8L}{\pi R^4}\right)$$

by means of which the measurable pressure ratio $P/(P - P_{\text{measurement capillary}})$ becomes equal to an expression consisting of geometric quantities. The term in parenthesis for the valve permits all sub-flow resistances to be matched (uniformity of the sub-flows) or specified deviations hereof to be adjusted during the regulating process over the gap width s for each of the n conveying lines. The sub-flows, present after the flow resistances are regulated, are inversely proportional to the flow resistance of the conveying line.

The invention described is used for indirectly regulating the flow in liquid chromatography equipment, as shown in FIG. 3 and realized in FIG. 2b. The chromatography column, which is filled with spherical particles, is to be regarded as the main flow resistance of the conveying lines. The flow resistance of a chromatography column can be described as follows:

$$R_{\text{chromatography column}} = \frac{\Delta P_{\text{chromatography column}}}{V_{\text{sub}}} = \frac{\chi \eta H}{d_k^2 D^2}$$

in which $\chi$ is a dimensionless constant, H is the height of the column, D is the diameter of the column and $d_k$ is the diameter of the particles.

For the flow resistance values $R_{\text{total}}$ in a conveying line, which are to be regulated, the following relationship can be formulated after the viscosity is eliminated:

$$R_{\text{total}} = \frac{P}{P - P_{\text{measuring capillary}}} = \frac{\pi r^4}{8l}\left(\frac{8l}{\pi r^4} + \frac{6G}{\pi s^3} + \frac{\chi H}{d_k^2 D^2}\right)$$

With the resulting total pressure ahead of the distribution $$P = \Delta P_{\text{measurement capillary}} + \Delta P_{\text{valve}} + \Delta P_{\text{pipeline}}$$

it is possible to write for the total flow resistance $R_{\text{total}}$ of the conveying line in question $$R_{\text{total}} = \frac{P}{V_{\text{sub}}} = \frac{8\eta l}{\pi r^4} + \frac{6\eta}{\pi s^3}G + \frac{8\eta L}{\pi R^4}$$

Since $$V_{\text{sub}} = \frac{\pi r^4}{8\eta l}\Delta P_{\text{measurement capillary}} = \frac{\pi r^4}{8\eta l}(P - P_{\text{measurement capillary}})$$

the following can be written for the total flow resistance of the conveying line:

$$R_{\text{total}} = \left(\frac{8\eta l}{\pi r^4}\right)\frac{P}{P - P_{\text{measurement capillary}}} = R_{\text{measurement capillary}} + R_{\text{valve}} + R_{\text{pipeline}}$$

If the temperature is the same everywhere in the equipment, the viscosity η=f(T)=const. can be eliminated from all the elements and the following relationship results $$\frac{P}{P - P_{\text{measurement capillaryl}}} \frac{\pi r^4}{8l}\left(\frac{8l}{\pi r^4} + \frac{6G}{\pi s^3} + \frac{8L}{\pi R^4}\right)$$

by means of which the measurable pressure ratio P/(P-P$_{measurement\ capillary}$) becomes equal to an expression consisting of geometric quantities.. The term in parenthesis for the valve permits all sub-flow resistances to be matched (uniformity of the sub-flows) or specified deviations hereof to be adjusted during the regulating process over the gap width s for each of the n conveying lines. The sub-flows, present after the flow resistances are regulated, are inversely proportional to the flow resistance of the conveying line.

The invention described is used for indirectly regulating the flow in liquid chromatography equipment, as shown in FIG. 3 and realized in FIG. 2b. The chromatography column, which is filled with spherical particles, is to be regarded as the main flow resistance of the conveying lines. The flow resistance of a chromatography column can be described as follows:

$$R_{\text{chromatography column}} = \frac{\Delta P_{\text{chromatography column}}}{V_{\text{sub}}} = \frac{\chi \eta H}{d_k^2 D^2}$$

in which $\chi$ is a dimensionless constant, H is the height of the column, D is the diameter of the column and $d_k$ is the diameter of the particles.

For the flow resistance values R$_{total}$ in a conveying line, which are to be regulated, the following relationship can be formulated after the viscosity is eliminated:

$$\frac{P}{P - P_{\text{measuring capillary}}} = \frac{\pi r^4}{8l}\left(\frac{8l}{\pi r^4} + \frac{6G}{\pi s^3} + \frac{\chi H}{d_k^2 D^2}\right)$$

The measurable pressure ratio P/(P-P$_{measurement\ capillary}$) here also becomes equal to an expression of geometric quantities. In this case, the valves are selected so that equalization of the flow resistance R$_{total}$ can be reached during the regulating process.

What is claimed is:

1. A method for regulating a conveying system for fluid media with several parallel conveying lines (11) with the proviso of a constant total conveyed flow, the conveying lines (11) being supplied from a single conveying unit (9), wherein the constant conveyed total flow is divided in the respective conveying lines (11) into specified sub-flows by regulating sub-flow resistances (1), which are ascertained continuously as a ratio of a total pressure value to a sub-flow value, in that the ascertained ratios, as actual values, are compared with a specified value for each conveying line (11) and, depending on the magnitude of the respective deviation between the actual value and the specified value, a regulation of the respective sub-flow resistance (1) and, with that, of the sub-flow of the fluid medium in the respective conveying line, takes place.

2. The method of claim 1, wherein the total flow is divided into precisely identical sub-flows.

3. The method of claim 1, wherein the total pressure value of the conveying system is measured at the inlet side and sub-flow values are measured directly in the conveying lines (11).

4. The method of claim 1, wherein the total pressure value of the conveying system is measured at the inlet side and sub-flow values are measured indirectly in the conveying lines (11).

5. The method of claim 1, wherein the specified value is determined by the ratio of a product of the total pressure and the number of conveying lines (11) to the total flow.

6. The method of claim 5, wherein, in the event that different sub-flows are specified, the specified value is multiplied by a factor corresponding to the specified sub-flow.

7. An apparatus for regulating individual sub-flows of a conveying system for fluid media with specification of a total flow, constantly conveyed, with several parallel conveying lines and a single conveying unit (9), wherein at least one total pressure measuring device (10), a distributor (8), at least one sub-flow measuring unit (D) and at least one valve (7) with a throttling site (B), as well as a data acquisition, processing and set value output module (C), are disposed in each conveying line (11.1 to 11.8) and connected over hardware and/or software functionally with one another and are suitable for regulating flow resistances (1) that are ascertained by forming ratios of a total pressure value to a sub-flow values as actual values, for comparing the actual values with specified nominal values and for putting out control values arising from these comparisons for regulation of respective sub-flow resistances (1).

8. The apparatus of claim 7, wherein the sub-flow measuring unit (D) has a measuring capillary (2) and a partial pressure measuring device (3).

9. The apparatus of claim 7, wherein the sub-flow measuring unit (D) has a measuring capillary (2) and two partial pressure measuring devices (3, 12).

10. The apparatus of claim 7, wherein the sub-flow measuring unit (D) has a measuring capillary (2) with a pressure difference measuring device.

11. The apparatus of claim 7, wherein the sub-flow measuring unit (D) has a flow meter.

12. The apparatus of claim 7, wherein the data acquisition, processing and set value output module (C) have an actual value determination (4), a nominal value delivery part (5), a comparison site (A) as well as a controller (6) with proportional and/or integral and/or differential control behavior.

13. The apparatus of claim 7, wherein the total pressure measuring device (10) is disposed at the output side of a conveying unit (9).

14. The apparatus of claim 7, wherein the flow resistances (1) are disposed at the output side of the distributor (8).

15. The apparatus of claim 7, wherein the throttling site (B) of the value (7) and the sub-flow measuring unit (D) are disposed in a conveying line between the total pressure meter (10) and serially to the flow resistance (1).

16. The apparatus of claim 7, wherein the valve (7) with the throttling site (B) and the sub-flow measuring unit (D) are disposed in a conveying line on the outlet side of the flow resistance (1).

17. The apparatus of claim 7, wherein the valve (7) with the throttling site (B) and the sub-flow measuring unit (D) are disposed on the inlet side of the flow resistance (1).

18. The apparatus of claim 7, wherein the valve (7) with the throttling site (B) is disposed on the outlet side and the sub-flow measuring unit (D) is disposed on the inlet side of the flow resistance (1).

19. The apparatus of claim 7, wherein the sub-flow measuring unit (D) is disposed on the outlet side and the valve (7) with the throttling site (B) on the inlet side of the flow resistance (1).

\* \* \* \* \*